United States Patent
McCaffrey et al.

(10) Patent No.: US 11,633,541 B2
(45) Date of Patent: Apr. 25, 2023

(54) CARTRIDGE HOLD-UP VOLUME REDUCTION

(71) Applicant: Insulet Corporation, Acton, MA (US)

(72) Inventors: Maureen McCaffrey, Boston, MA (US); David Nazzaro, Groveland, MA (US); Ian McLaughlin, Groton, MA (US); Simon Kozin, Lexington, MA (US)

(73) Assignee: INSULET CORPORATION, Acton, MA (US)

( * ) Notice: Subject to any disclaimer, the term of this patent is extended or adjusted under 35 U.S.C. 154(b) by 523 days.

(21) Appl. No.: 16/794,689

(22) Filed: Feb. 19, 2020

(65) Prior Publication Data

US 2020/0179608 A1    Jun. 11, 2020

Related U.S. Application Data

(63) Continuation of application No. 15/875,115, filed on Jan. 19, 2018, now Pat. No. 10,603,440.

(51) Int. Cl.
*A61M 37/00*     (2006.01)
*A61M 5/28*      (2006.01)
(Continued)

(52) U.S. Cl.
CPC ............ *A61M 5/285* (2013.01); *A61M 5/142* (2013.01); *A61M 5/2455* (2013.01);
(Continued)

(58) Field of Classification Search
CPC .. A61M 5/2455; A61M 5/2422; A61M 5/285; A61M 5/34; A61M 2005/31516; A61J 1/2089

See application file for complete search history.

(56) References Cited

U.S. PATENT DOCUMENTS

| | | |
|---|---|---|
| 1,441,508 A | 1/1923 | Jensen |
| 2,198,666 A | 4/1940 | Gruskin |

(Continued)

FOREIGN PATENT DOCUMENTS

| | | |
|---|---|---|
| CA | 606281 A | 10/1960 |
| CN | 1375338 A | 10/2002 |

(Continued)

OTHER PUBLICATIONS

Schott web-page image from Jul. 9, 2016, https://www.us.schott.com/pharmaceutical_packaging/english/products/cartrid es.html.
(Continued)

*Primary Examiner* — Rebecca E Eisenberg
(74) *Attorney, Agent, or Firm* — Goodwin Procter LLP

(57) ABSTRACT

Drug delivery systems with reduced hold-up volumes are provided. The drug delivery systems include a cartridge configured to hold a liquid drug. A cartridge stopper is positioned in a first portion of the cartridge. A needle guide component is positioned within the cartridge stopper. A needle is positioned within a central opening of the needle guide. A plunger is positioned in a second portion of the cartridge. The plunger includes a fluid path pocket facing and aligned with the central opening of the needle guide component. The plunger is driven toward the cartridge stopper to expel the liquid drug from the cartridge through the needle. An end of the needle can be positioned within the fluid path pocket when the plunger is pushed against the cartridge stopper, ensuring that only a small volume of the liquid drug remains in the cartridge when delivery of the liquid drug is completed.

18 Claims, 11 Drawing Sheets

Related U.S. Application Data

(60) Provisional application No. 62/549,488, filed on Aug. 24, 2017, provisional application No. 62/453,065, filed on Feb. 1, 2017, provisional application No. 62/448,222, filed on Jan. 19, 2017.

(51) Int. Cl.
| | |
|---|---|
| *A61M 5/24* | (2006.01) |
| *A61M 5/34* | (2006.01) |
| *A61M 5/32* | (2006.01) |
| *A61M 5/315* | (2006.01) |
| *A61M 5/142* | (2006.01) |
| *A61J 1/20* | (2006.01) |

(52) U.S. Cl.
CPC ...... *A61M 5/2466* (2013.01); *A61M 5/31573* (2013.01); *A61M 5/3293* (2013.01); *A61M 5/34* (2013.01); *A61J 1/2089* (2013.01); *A61M 2005/31516* (2013.01)

(56) References Cited

U.S. PATENT DOCUMENTS

| | | | |
|---|---|---|---|
| 2,752,918 A | | 7/1956 | Uytenbogaart et al. |
| 3,176,712 A | | 4/1965 | Ramsden |
| 3,297,260 A | | 1/1967 | Barlow |
| 3,464,359 A | | 9/1969 | King |
| 3,885,662 A | | 5/1975 | Schaefer |
| 3,946,732 A | * | 3/1976 | Hurscham ............ A61J 1/2093 604/88 |
| 3,947,692 A | | 3/1976 | Payne |
| 3,993,061 A | | 11/1976 | OLeary |
| 4,055,177 A | * | 10/1977 | Cohen ............... A61M 5/31596 604/88 |
| 4,108,177 A | | 8/1978 | Pistor |
| 4,152,098 A | | 5/1979 | Moody et al. |
| 4,210,173 A | | 7/1980 | Choksi et al. |
| 4,221,219 A | | 9/1980 | Tucker |
| 4,257,324 A | | 3/1981 | Stefansson et al. |
| 4,268,150 A | | 5/1981 | Chen |
| 4,277,226 A | | 7/1981 | Archibald |
| 4,313,439 A | | 2/1982 | Babb et al. |
| 4,371,790 A | | 2/1983 | Manning et al. |
| 4,417,889 A | | 11/1983 | Choi |
| 4,424,720 A | | 1/1984 | Bucchianeri |
| 4,435,173 A | | 3/1984 | Siposs et al. |
| 4,475,905 A | | 10/1984 | Himmelstrup |
| 4,498,843 A | | 2/1985 | Schneider et al. |
| 4,507,115 A | | 3/1985 | Kambara et al. |
| 4,551,134 A | | 11/1985 | Slavik et al. |
| 4,562,751 A | | 1/1986 | Nason et al. |
| 4,567,549 A | | 1/1986 | Lemme |
| 4,585,439 A | | 4/1986 | Michel |
| 4,601,707 A | | 7/1986 | Albisser et al. |
| 4,634,427 A | | 1/1987 | Hannula et al. |
| 4,671,429 A | | 6/1987 | Spaanderman et al. |
| 4,678,408 A | | 7/1987 | Nason et al. |
| 4,684,368 A | | 8/1987 | Kenyon |
| 4,685,903 A | | 8/1987 | Cable et al. |
| 4,755,169 A | | 7/1988 | Sarnoff et al. |
| 4,766,889 A | | 8/1988 | Trick et al. |
| 4,808,161 A | | 2/1989 | Kamen |
| 4,846,797 A | | 7/1989 | Howson et al. |
| 4,858,619 A | | 8/1989 | Toth |
| 4,898,579 A | | 2/1990 | Groshong et al. |
| 4,908,017 A | | 3/1990 | Howson et al. |
| 4,944,659 A | | 7/1990 | Labbe et al. |
| 4,969,874 A | | 11/1990 | Michel et al. |
| 4,991,743 A | | 2/1991 | Walker |
| 5,007,458 A | | 4/1991 | Marcus et al. |
| 5,020,325 A | | 6/1991 | Henault |
| 5,062,841 A | | 11/1991 | Siegel |
| 5,147,311 A | | 9/1992 | Pickhard |
| 5,178,609 A | | 1/1993 | Ishikawa |
| 5,205,819 A | | 4/1993 | Ross et al. |
| 5,213,483 A | | 5/1993 | Flaherty et al. |
| 5,222,362 A | | 6/1993 | Maus et al. |
| 5,236,416 A | | 8/1993 | McDaniel et al. |
| 5,261,882 A | | 11/1993 | Sealfon |
| 5,261,884 A | | 11/1993 | Stern et al. |
| 5,277,338 A | | 1/1994 | Divall |
| 5,281,202 A | | 1/1994 | Weber et al. |
| 5,346,476 A | | 9/1994 | Elson |
| 5,364,342 A | | 11/1994 | Beuchat et al. |
| 5,388,615 A | | 2/1995 | Edlund et al. |
| 5,433,710 A | | 7/1995 | VanAntwerp et al. |
| 5,503,628 A | | 4/1996 | Fetters et al. |
| 5,520,661 A | | 5/1996 | Lal et al. |
| 5,533,389 A | | 7/1996 | Kamen et al. |
| 5,582,593 A | | 12/1996 | Hultman |
| 5,618,269 A | | 4/1997 | Jacobsen et al. |
| 5,628,309 A | | 5/1997 | Brown |
| 5,637,095 A | | 6/1997 | Nason et al. |
| 5,665,070 A | | 9/1997 | McPhee |
| 5,713,875 A | | 2/1998 | Tanner, II |
| 5,747,350 A | | 5/1998 | Sattler |
| 5,748,827 A | | 5/1998 | Holl et al. |
| 5,776,103 A | | 7/1998 | Kriesel et al. |
| 5,779,676 A | | 7/1998 | Kriesel et al. |
| 5,785,688 A | | 7/1998 | Joshi et al. |
| 5,797,881 A | | 8/1998 | Gadot |
| 5,800,397 A | | 9/1998 | Wilson et al. |
| 5,807,075 A | | 9/1998 | Jacobsen et al. |
| 5,839,467 A | | 11/1998 | Saaski et al. |
| 5,891,097 A | | 4/1999 | Saito et al. |
| 5,897,530 A | | 4/1999 | Jackson |
| 5,906,597 A | | 5/1999 | McPhee |
| 5,911,716 A | | 6/1999 | Rake et al. |
| 5,919,167 A | | 7/1999 | Mulhauser et al. |
| 5,957,890 A | | 9/1999 | Mann et al. |
| 5,961,492 A | | 10/1999 | Kriesel et al. |
| 5,971,963 A | | 10/1999 | Choi |
| 6,019,747 A | | 2/2000 | McPhee |
| 6,050,457 A | | 4/2000 | Arnold et al. |
| 6,068,615 A | | 7/2000 | Brown et al. |
| 6,159,188 A | | 12/2000 | Laibovitz et al. |
| 6,174,300 B1 | | 1/2001 | Kriesel et al. |
| 6,190,359 B1 | | 2/2001 | Heruth |
| 6,200,293 B1 | | 3/2001 | Kriesel et al. |
| 6,352,522 B1 | | 3/2002 | Kim et al. |
| 6,363,609 B1 | | 4/2002 | Pickren |
| 6,375,638 B2 | | 4/2002 | Nason et al. |
| 6,474,219 B2 | | 11/2002 | Klitmose et al. |
| 6,485,461 B1 | | 11/2002 | Mason et al. |
| 6,485,462 B1 | | 11/2002 | Kriesel |
| 6,488,652 B1 | | 12/2002 | Weijand et al. |
| 6,520,936 B1 | | 2/2003 | Mann |
| 6,527,744 B1 | | 3/2003 | Kriesel et al. |
| 6,537,249 B2 | | 3/2003 | Kriesell et al. |
| 6,539,286 B1 | | 3/2003 | Jiang |
| 6,569,115 B1 | | 5/2003 | Barker et al. |
| 6,595,956 B1 | | 7/2003 | Gross et al. |
| 6,656,158 B2 | | 12/2003 | Mahoney et al. |
| 6,699,218 B2 | | 3/2004 | Flaherty et al. |
| 6,723,072 B2 | | 4/2004 | Flaherty et al. |
| 6,740,059 B2 | | 5/2004 | Flaherty |
| 6,749,407 B2 | | 6/2004 | Xie et al. |
| 6,851,260 B2 | | 2/2005 | Mernoe |
| 6,883,778 B1 | | 4/2005 | Newton et al. |
| 7,018,360 B2 | | 3/2006 | Flaherty et al. |
| 7,104,275 B2 | | 9/2006 | Dille |
| 7,128,727 B2 | | 10/2006 | Flaherty et al. |
| 7,137,964 B2 | | 11/2006 | Flaherty |
| 7,144,384 B2 | | 12/2006 | Gorman et al. |
| 7,160,272 B1 | | 1/2007 | Eyal et al. |
| 7,771,392 B2 | | 8/2010 | De Polo et al. |
| 7,914,499 B2 | | 3/2011 | Gonnelli et al. |
| 7,951,114 B2 | | 5/2011 | Rush et al. |
| 8,267,921 B2 | | 9/2012 | Yodfat et al. |
| 8,382,703 B1 | | 2/2013 | Abdelaal |
| 8,499,913 B2 | | 8/2013 | Gunter |
| 8,905,995 B2 | | 12/2014 | Mernoe |
| 8,920,376 B2 | | 12/2014 | Caffey et al. |

(56) References Cited

U.S. PATENT DOCUMENTS

| | | |
|---|---|---|
| 8,939,935 B2 | 1/2015 | OConnor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 10,441,723 B2 | 10/2019 | Nazzaro |
| 10,695,485 B2 | 6/2020 | Nazzaro |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | DAntonio et al. |
| 2003/0055380 A1 | 3/2003 | Flaherty |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0073236 A1 | 3/2007 | Mernoe et al. |
| 2007/0088271 A1 | 4/2007 | Richards |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0243211 A1 | 10/2008 | Cartwright et al. |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0073620 A1 | 3/2011 | Verrilli |
| 2011/0144586 A1 | 6/2011 | Michaud et al. |
| 2011/0180480 A1 | 7/2011 | Kloeffel et al. |
| 2011/0230833 A1 | 9/2011 | Landman et al. |
| 2012/0078161 A1 | 3/2012 | Masterson et al. |
| 2012/0172817 A1 | 7/2012 | Bruggemann et al. |
| 2012/0209207 A1 | 8/2012 | Gray et al. |
| 2013/0006213 A1 | 1/2013 | Arnitz et al. |
| 2013/0017099 A1 | 1/2013 | Genoud |
| 2013/0064701 A1 | 3/2013 | Konishi |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0296792 A1 | 11/2013 | Cabiri |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamen |
| 2016/0055842 A1 | 2/2016 | DeFranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213851 A1 | 7/2016 | Weibel et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0345931 A1 | 11/2020 | Gray et al. |

FOREIGN PATENT DOCUMENTS

| | | |
|---|---|---|
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | H06296690 A | 10/1994 |
| JP | H08238324 A | 9/1996 |
| JP | 2004247271 A | 9/2004 |
| JP | 2004274719 A | 9/2004 |
| JP | 2005188355 A | 7/2005 |
| JP | 2006159228 A | 6/2006 |
| JP | 6098988 B2 | 9/2006 |

(56) References Cited

FOREIGN PATENT DOCUMENTS

| | | |
|---|---|---|
| JP | 2006249130 A | 9/2006 |
| JP | 2009514580 A | 4/2009 |
| JP | 2017513577 A | 6/2017 |
| NL | 1019126 C1 | 4/2003 |
| WO | 8101658 A1 | 6/1981 |
| WO | 8606796 A1 | 11/1986 |
| WO | 9320864 A1 | 10/1993 |
| WO | 9415660 A1 | 7/1994 |
| WO | 9855073 A1 | 12/1998 |
| WO | 9856293 A1 | 12/1998 |
| WO | 9910040 A1 | 3/1999 |
| WO | 9910049 A1 | 3/1999 |
| WO | 9962576 A1 | 12/1999 |
| WO | 0029047 A1 | 5/2000 |
| WO | 0178812 A1 | 10/2001 |
| WO | 0220073 A2 | 3/2002 |
| WO | 0226282 A2 | 4/2002 |
| WO | 2002076535 A1 | 4/2002 |
| WO | 2003097133 A1 | 4/2002 |
| WO | 02068823 A1 | 9/2002 |
| WO | 2004032994 A2 | 4/2004 |
| WO | 2004056412 A2 | 7/2004 |
| WO | 2004110526 A1 | 12/2004 |
| WO | 2007066152 A2 | 6/2007 |
| WO | 2008133702 A1 | 11/2008 |
| WO | 2009039203 A2 | 3/2009 |
| WO | 2009141005 A1 | 11/2009 |
| WO | 2010022069 A2 | 2/2010 |
| WO | 2010077279 A1 | 7/2010 |
| WO | 2010139793 A1 | 12/2010 |
| WO | 2011010198 A2 | 1/2011 |
| WO | 2011031458 A1 | 3/2011 |
| WO | 2011069935 A2 | 6/2011 |
| WO | 2011075042 A1 | 6/2011 |
| WO | 2011133823 A1 | 10/2011 |
| WO | 2012073032 A1 | 6/2012 |
| WO | 2013050535 A2 | 4/2013 |
| WO | 2013137893 A1 | 9/2013 |
| WO | 2013149186 A1 | 10/2013 |
| WO | 2014029416 A1 | 2/2014 |
| WO | 2014149357 A1 | 9/2014 |
| WO | 2014179774 A1 | 11/2014 |
| WO | 2015032772 A1 | 3/2015 |
| WO | 2015048791 A1 | 4/2015 |
| WO | 2015081337 A2 | 6/2015 |
| WO | 2015117854 A1 | 8/2015 |
| WO | 2015167201 A1 | 11/2015 |
| WO | 2015177082 A1 | 11/2015 |
| WO | 2017148855 A1 | 9/2017 |
| WO | 2017187177 A1 | 11/2017 |
| WO | 2021016452 A1 | 1/2021 |

OTHER PUBLICATIONS

International Search Report and Written Opinion for Application No. PCT/US2019/059854, dated Aug. 26, 2020, 15 pages.
European Search Report and Written Opinion for the European Patent Application No. EP20174878, dated Sep. 29, 2020, 8 pages.
International Search Report and Written Opinion for PCT/US2018/014351, dated Jun. 4, 2018, 9 pages.
"Lind, et al. "Linear Motion Miniature Actuators."" Paper presented at the 2nd Tampere International Conference onMachine Automation, Tampere, Finland (Sep. 1998).
Author unknown, ""The Animas R-1000 Insulin Pump—Animas Corporation intends to exit the insulin pump businessand discontinue the manufacturing and sale of Animas® Vibe® and One Touch Ping® insulin pumps."" [online],Dec. 1999 [retrieved on Jan. 8, 2019]. Retrieved from the Internet URL: http://www.animaspatientsupport.com/.
Author unknown, CeramTec ""Discover the Electro Ceramic Products CeramTec acquired from Morgan Advanced Materials"" [online], Mar. 1, 2001 [retrieved on Jan. 8, 2019. Retrieved from the Internet URL: http://www.morgantechnicalceramics.com/.
Vaughan, M.E., ""The Design, Fabrication, and Modeling of a Piezoelectric Linear Motor."" Master's thesis,Virginia Polytechnic Institute and State University, VA. (2001).
Galante, et al., "Design, Modeling, and Performance of a High Force Piezoelectric Inchworm Motor," Journal of Intelligent Material Systems and Structures, vol. 10, 962-972 (1999).
International Search Report and Written Opinion for Interantional application No. PCT/US2017/055054, dated Jan. 25, 2018, 14 pages.
International Search Report and Written Opinion for International application No. PCT/US2018/045155, dated Oct. 15, 2018, 12 pages.
International Preliminary Report on Patentability for International application No. PCT/US2017/034811 dated Nov. 27, 2018 10 pages.
International Preliminary Report on Patentability for the International Patent Application No. PCT/US2017/046508 dated Feb. 12, 2019 10 pp.
International Search Report and Written Opinion for International application No. PCT/US2017/046508, dated Jan. 17, 2018, 14 pages.
International Search Report and Written Opinion for International application No. PCT/US2017/046777, dated Dec. 13, 2017, 14 pages.
International Search Report and Written Opinion for International application No. PCT/US2017/046737, dated Dec. 14, 2017, 11 pages.
International Search Report and Written Opinion for International application No. PCT/US2017/034814, dated Oct. 11, 2017, 16 pages.
European Search Report and Written Opinion for the European Patent Application No. EP19177571, dated Oct. 30, 2019, 8 pages.
International Preliminary Report on Patentability for the International Patent Application No. PCT/US 1814351, dated Aug. 1, 2019, 6 pages.
International Preliminary Report on Patentability for the International Patent Application No. PCT/US2017/046777, dated Feb. 19, 2019, 8 pages.
International Preliminary Report on Patentability for the International Patent Application No. PCT/US2017/046737, dated Feb. 19, 2019, 8 pages.
International Preliminary Report on Patentability for the International Patent Application No. PCT/US2017/055054, dated Apr. 9, 2019, 8 pages.
International Search Report and Written Opinion for application No. PCT/US2017/034811, dated Oct. 18, 2017, 15 pages.
EPO Search Report dated Nov. 11, 2015, received in corresponding Application No. 13768938.6, 7 pgs.
PCT International Search Report and Written Opinion dated Aug. 6, 2013, received in corresponding PCT Application No. PCT/US13/34674, pp. 1-19.
International Search Report and Written Opinion for International application No. PCT/GB2007/004073, dated Jan. 31, 2008.
International Search Report and Written Opinion for the International Patent Application No. PCT/US2019/063615, dated May 3, 2020, 16 pages.
International Preliminary Report on Patentability for the International Patent Application No. PCT/US2018/045155, dated Feb. 13, 2020, 10 pages.
International Search Report and Written Opinion for the International Patent Application No. PCT/US2019/035756, dated Jul. 31, 2019, 11 pages.
International Search Report and Written Opinion for the International Patent Application No. PCT/US2021/055581, dated Feb. 8, 2022, 19 pages.
International Search Report and Written Opinion, Application No. PCT/US2022/016713, dated Aug. 5, 2022, 19 pages.
International Search Report and Written Opinion for International Patent Application No. PCT/US2022/011356, dated Apr. 29, 2022, 19 pages.

(56) References Cited

OTHER PUBLICATIONS

International Search Report and Written Opinion for International Patent Application No. PCT/US2022/029012, dated Aug. 19, 2022, 12 pages.

* cited by examiner

CARTRIDGE HOLD-UP VOLUME REDUCTION

CROSS-REFERENCE TO RELATED APPLICATIONS

This application is a continuation of U.S. Non-Provisional application Ser. No. 15/875,115, filed Jan. 19, 2018, which claims the benefit of U.S. Provisional Application No. 62/448,222, filed Jan. 19, 2017, U.S. Provisional Application No. 62/453,065, filed Feb. 1, 2017, and U.S. Provisional Application No. 62/549,488, filed Aug. 24, 2017, each of which is incorporated herein by reference in its entirety.

TECHNICAL FIELD

Embodiments generally relate to medication delivery. More particularly, embodiments relate to reducing hold-up volume for drug delivery systems.

BACKGROUND

An on-body delivery system (OBDS) is often used to deliver drug dosages to a user. Many OBDSs use cartridges to hold a liquid drug that is expelled from the cartridge when a portion of the liquid drug is desired to be delivered to the user. Many conventional OBDSs and associated cartridges are not capable of delivering all of the stored liquid drug to the user. Specifically, relatively significant amounts of the liquid drug can remain inside of the pre-filled cartridge when the OBDS completes full delivery. The undelivered amount of the liquid drug is wasted and for expensive drugs can increase costs to various parties, including the user. Accordingly, there is a need for an OBDS, drug delivery system and/or device, and/or cartridge having reduced amounts of a liquid drug remaining after delivery to reduce waste and reduce costs to various parties, including the user.

DETAILED DESCRIPTION

This disclosure presents various systems, components, and methods related to a drug delivery system and/or device. Each of the systems, components, and methods disclosed herein provides one or more advantages over conventional systems, components, and methods.

Various embodiments provide drug delivery systems with reduced hold-up volumes. The drug delivery systems include a cartridge configured to hold a liquid drug. A cartridge stopper is positioned in a first portion of the cartridge having a first diameter and forms a first seal for the liquid drug. A needle guide component is positioned within the cartridge stopper. A needle is positioned within a central opening of the needle guide. A plunger is positioned in a second portion of the cartridge having a second diameter, with the second diameter larger than the first diameter. The plunger forms a second seal for the liquid drug. The plunger includes a fluid path pocket facing and aligned with the central opening of the needle guide component. The needle pierces the cartridge stopper to be coupled to the liquid drug. The plunger is driven toward the cartridge stopper to expel the liquid drug from the cartridge through the needle. An end of the needle can be positioned within the fluid path pocket when the plunger is pushed against the cartridge stopper, ensuring that only a small volume of the liquid drug remains in the cartridge (e.g., within a portion of the fluid path pocket) when delivery of the liquid drug is completed. As a result, a reduced amount of the liquid drug remains within the cartridge when delivery is complete.

Figure 1A:
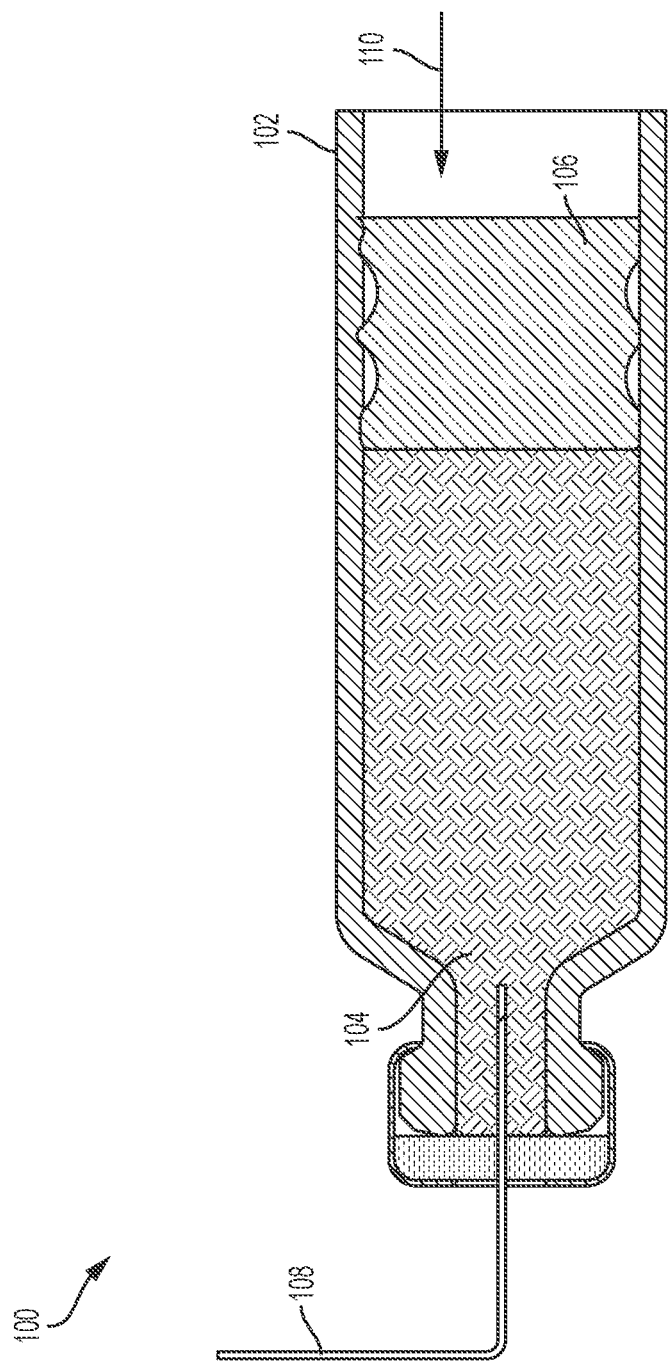
FIG. 1A illustrates a first view of a conventional drug delivery system.

FIG. 1A illustrates a conventional drug delivery system 100. The drug delivery system 100 includes a drug container or cartridge 102. The cartridge 102 can hold or store a liquid drug 104. A plunger 106 can be positioned within the cartridge 102. A needle 108 can be positioned within the cartridge 102 and coupled to the liquid drug 104.

To expel the liquid drug 104 from the cartridge 102, the plunger 106 can be moved in a direction 110 toward the needle 108. In doing so, the plunger 106 can force a portion of the liquid drug 104 through the needle 108 and out of the cartridge 102. As the plunger 106 moves closer to the needle 108, more of the liquid drug 104 can be expelled from the cartridge 102.

Figure 1B:
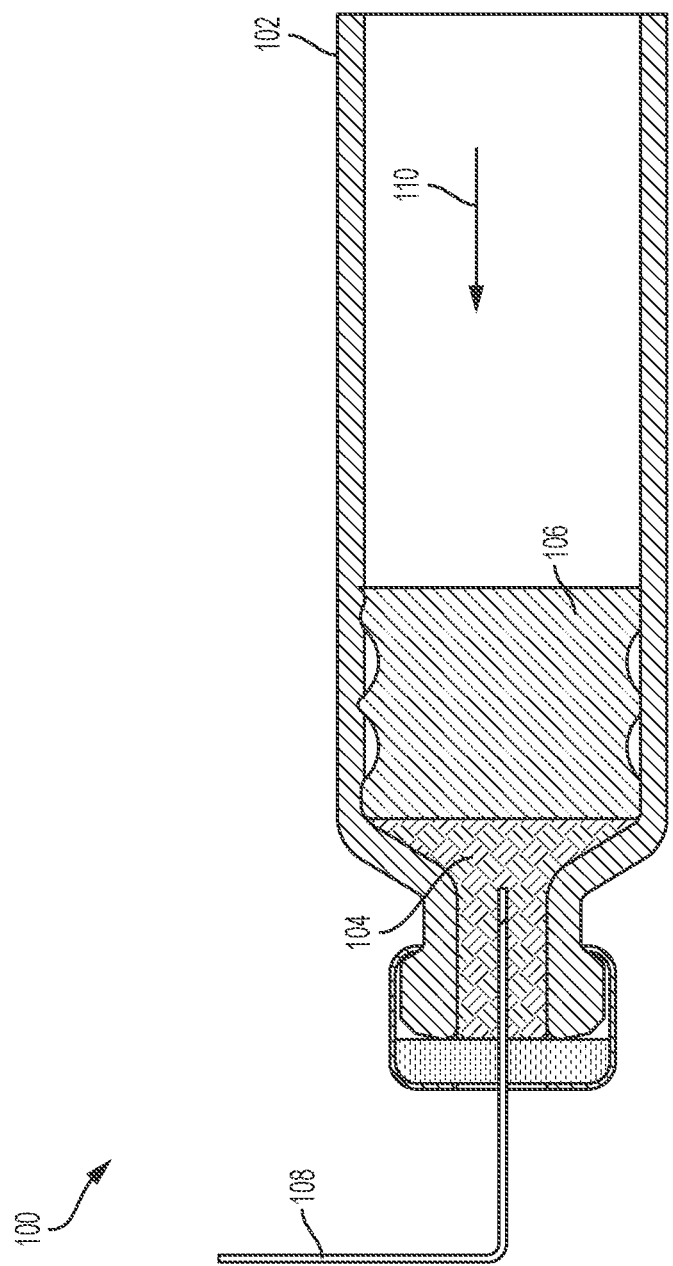
FIG. 1B illustrates a second view of the conventional drug delivery system of FIG. 1A.

FIG. 1B illustrates a subsequent stage of operation of the drug delivery system 100 relative to the depiction of the drug delivery system 100 in FIG. 1A. As shown in FIG. 1B, the plunger 106 is positioned adjacent to a neck of the cartridge 102 and cannot be advanced any further in the direction 110. As a result, a portion of the liquid drug 104 remains in the cartridge 102 as shown in FIG. 1B. That is, the liquid drug 104 remaining in the cartridge 102 cannot be expelled from the cartridge 102 by the plunger 106. The amount of space occupied by this portion of the liquid drug 104 that remains effectively trapped in the cartridge 102 (or the amount or volume of the remaining liquid drug 104 itself) can be considered to be a hold-up volume (or portion thereof) of the cartridge 102 and/or the drug delivery system 100. As will be appreciated by one of ordinary skill in the art, in additional to the amount of space in the cartridge 102, the entire fluid path (e.g., the needle) can also be considered to contribute to hold-up and/or to contribute to the hold-up volume of the system.

Hold-up volume can represent the amount of space that can be occupied by a liquid drug that cannot be expelled and can include the volume of liquid drug that cannot be expelled. As shown in FIGS. 1A and 1B, the arrangement and shapes of the components of the drug delivery system 100 contribute to the size and shape of the resulting hold-up volume. Since the hold-up volume retains a portion of the liquid drug 104 that cannot be expelled, reduction and minimization of the hold-up volume is desirable. In general, the hold-up volume represents a wasted or unused portion of the liquid drug 104. For very expensive drugs, the wasted amount of the liquid drug 104 can be very costly, which can be passed along to the user, insurance company, or other purchaser of the drug delivery system 100.

Since a portion of the stored liquid drug 104 may be trapped inside of the drug delivery system 100 (or at least not delivered to the user), then the amount of liquid drug 104 used to fill the cartridge 102 may be greater than the amount of liquid drug 104 that corresponds to the dose of the user. As explained above, this "over-filling" of the liquid drug 104 for the user can add costs to the drug delivery system 100. In addition to this problem, air can be introduced into the drug delivery system 100 during typical filling processes associated with a pre-filled device such as the cartridge 102 and/or the drug delivery system 100. The introduced air is typically addressed in a number of ways. For example, the air may be purged out, which can add complexity and cost to the drug delivery system and/or burden on the user. Alternatively, the air can be delivered to the user. Lastly, the air can be trapped within the drug delivery device 100.

Since a body-worn device (e.g., an OBDS) is multi-oriented, depending on where and how it is attached to the user's body, air will move within the container that stores a liquid drug (e.g., within the cartridge 102 holding the liquid drug 104). In some instances, when air is trapped within the body-worn device and the outlet of the body-worn device is facing down, gravity may cause the heavier liquid drug out of the device prior to the air. In other instances, when air is trapped within the body-worn device and the outlet of the body-worn device is facing up, the air may be delivered first and a portion of the liquid drug may trapped within the device as part of the hold-up volume. Because of these various orientations of the body-worn device and their impact on whether air or liquid drug will be delivered to the patient, embodiments as described herein improve dose accuracy by reducing hold-up volume.

Dose accuracy can be affected when the ratio of hold-up volume to fill volume exceeds approximately 3-5%, with the dose accuracy being further negatively affected as this ration increases. For example, if a dose within 5% of 1 mL of a drug is desired using a device having a hold-up volume of 0.2 mL, then the desired dose accuracy is not possible. Accordingly, in addition to reducing wastes, it is desired to reduce hold-up volumes to achieve desired dosing accuracies and/or to achieve industry standard dose accuracy requirements.

Figure 2:
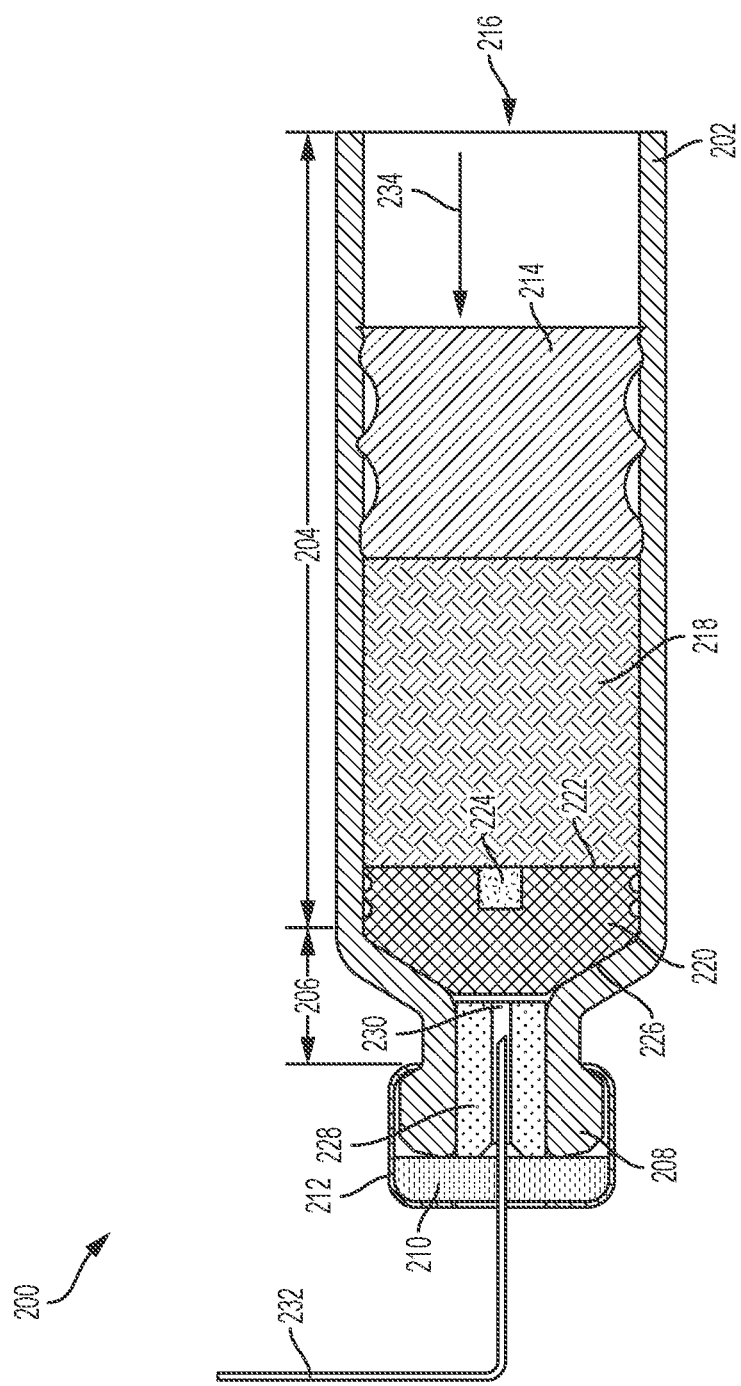
FIG. 2 illustrates a first view of a first exemplary drug delivery system.

FIG. 2 illustrates a first exemplary drug delivery system 200 for providing a reduced hold-up volume. The drug delivery system 200 can efficiently expel the liquid drug it contains while reducing amounts of the liquid drug retained by the drug delivery system 200 after use. The reduced hold-up volume provided by the drug delivery system 200 can improve dosing accuracy. FIG. 2 can represent a cross-sectional view of the drug delivery system 200. In various embodiments, the drug delivery system 200 can provide a ratio of hold-up volume to fill volume that is less 5% or less than 3%.

As shown in FIG. 2, the drug delivery system includes a drug container or cartridge 202. In various embodiments, the cartridge 202 can be an International Organization for Standardization (ISO) standard cartridge 202. In various embodiments, the cartridge 202 can be a custom design or customized cartridge 202. The cartridge 202 can comprise any suitable material such as, for example, metal, plastic, or glass, or any combination thereof. The cartridge 202 can include a main body component 204, a neck component 206, and a top component 208.

The cartridge 202 can generally be cylindrically-shaped with a diameter of the main body component 204 being substantially constant and larger than a diameter of the top component 208. The neck component 206 can have a variable diameter that transitions from a diameter corresponding to the diameter of the main body component 204 to the diameter of the top component 208. The variable diameter portion of the neck component 206 can be considered a transitional portion of the cartridge 202 where the wider main body component 204 transitions to the narrower top component 208.

The top component 208 can be sealed by a septum 210 and a crimp 212. The septum 210 can be positioned adjacent to and/or over the top component 208 (e.g., over an opening in the top component 208). The crimp 212 can be positioned around the septum 210 and the top component 208 to tightly fit the septum 210 against the top component 208. The septum 210 can comprise any suitable material such as, for example, metal or plastic, or any combination thereof. The crimp 212 can comprise any suitable material such as, for example, metal or plastic, or any combination thereof. The septum 210 and the crimp 212 can form at least one seal of the cartridge 202.

A second seal of the cartridge 202 can be formed by a plunger 214. The plunger 214 can comprise any suitable material such as, for example, plastic or rubber. The plunger 214 can be positioned within the main body component 204. The plunger 214 can be positioned into the main body component 204 through an opening 216 of the cartridge 202.

A drug 218 can be stored or held in the cartridge 202. The drug 218 can be a liquid drug. The drug 218 can be any therapeutic agent and/or medicine. The drug 218 can be stored within the main body component 204. The plunger 214 can be positioned to retain or seal the liquid drug 218 within the cartridge 202.

As further shown in FIG. 2, the drug delivery system 200 can also include a cartridge stopper 220. The cartridge stopper 220 can be positioned within any portion of the main body component 204 and/or the neck component 206. In various embodiments, the cartridge stopper 220 can be positioned within a portion of the neck component 206 and an adjacent portion of the main body component 204. The cartridge stopper 220 can include a first side 222 that is substantially flat or planar. The first side 222 can be coupled to the liquid drug 218 and can be facing the plunger 214. The first side 222 can include a fluid path pocket 224. The fluid path pocket 224 can comprise a hole or opening within the cartridge stopper 220, extending from the first side 222 into the cartridge stopper 220. The fluid path pocket 224 can be positioned at an approximate center of the cartridge stopper 220 (e.g., aligned with a center of the first side 222 and/or aligned with a central axis of the cartridge stopper 220).

A second side 226 of the cartridge stopper 220 can be shaped to fit within the transition region of the neck component 206. The second side 226 can face the top component 208 of the cartridge 202. In various embodiments, the second side 226 can be shaped to taper from a relatively wider diameter (e.g., a diameter of the main body component 204) to a relatively narrower diameter (e.g., a diameter of the narrowest portion of the neck component 206). The cartridge stopper 220 can also form a seal for the liquid drug 218 as shown in FIG. 2. The cartridge stopper 220 can be generally cylindrical-shaped and can be formed of any suitable material such as, for example, a plastic or rubber.

As shown in FIG. 2, an outer portion of the cartridge stopper 220 can include sealing features (e.g., sealing glands). In various embodiments, the cartridge stopper 220 can include any number of such sealing features that can be varied based on application. As further shown in FIG. 2, the liquid drug 218 is retained within the cartridge 202 by seals provided by the cartridge stopper 220 and the plunger 214.

The drug delivery system 200 can further include a needle insertion guide 228. The needle insertion guide 228 can be generally cylindrically-shaped and can be positioned within the top component 208 and the neck component 206. The needle insertion component 228 can comprise any suitable material such as, for example, metal, stainless steel, plastic, or a polymer, or any combination thereof.

The needle insertion guide 228 can include an opening or hole 230. The opening 230 can extend along an entire length of the needle insertion guide 228. The opening 230 can provide an area for a needle 232 to be guided through the top component 208 and the neck component 206. To reach the liquid drug 218, the needle 232 can be inserted through the crimp 212 and the septum 210 and into the opening 230 of the needle insertion guide 228. The needle 232 can then be inserted further into the cartridge 202 by subsequently piercing the cartridge stopper 220. Lastly, an end of the needle 232 can be inserted so as to be positioned within the fluid path pocket 224.

When the needle 232 is inserted with an end positioned within the fluid path pocket 224, the plunger 214 can be used to expel the liquid drug 218 from the cartridge 202. For example, the plunger 214 can be moved in a direction 234 toward the cartridge stopper 222. In doing so, the liquid drug 218 can be forced out of the cartridge 202 through the needle 232. The plunger 214 can be advanced in the direction 234 until the plunger 214 is adjacent to the first side 222 of the cartridge stopper 220. By maintaining the end of the needle 232 within the fluid path pocket 224, the plunger 214 can be pressed up against the first side 222 without damaging the needle 232 or disturbing the positioning of the needle 232.

As shown in FIG. 2, the fluid path pocket 224 can be positioned with a center of the cartridge stopper 220. In various embodiments, the fluid path pocket 224 can be aligned with the opening 230 of the needle insertion guide 228. This opening 230 guides the needle 232 such that as the needle 232 is inserted further into the cartridge 202, the needle 232 will reach the fluid path pocket 224.

FIG. 2 can represent a stage of operation of the drug delivery system 200 prior to expelling the liquid drug 218 from the cartridge 202 (e.g., prior to activation of the drug delivery system 200). As shown in FIG. 2, the needle 232 has pierced the septum 210 and is partially inserted into the needle insertion guide 228 but has not yet reached or pierced the cartridge stopper 220. In a subsequent stage of operation, after the end of the needle 232 is inserted into the fluid path pocket 224, the plunger 214 can be advanced in the direction 234 to expel the liquid drug 218 from the cartridge 202.

In various embodiments, the main body component 204 of the cartridge 202 can have a first diameter that is substantially constant across an entire length of the main body component 204. Further, the top component 208 and the neck component 206 of the cartridge 202 can have a smaller, second diameter. The neck component 206 can further include a region that transitions from the smaller or narrower region or portion of the cartridge 202 of the second diameter to the larger or wider region or portion of the cartridge 202 of the first diameter. In various embodiments, the top component 208 and the neck component 206 can together be considered to be a necked area or the neck component 206 of the cartridge 202—which transitions from the larger, first diameter to the smaller, second diameter.

Figure 3:
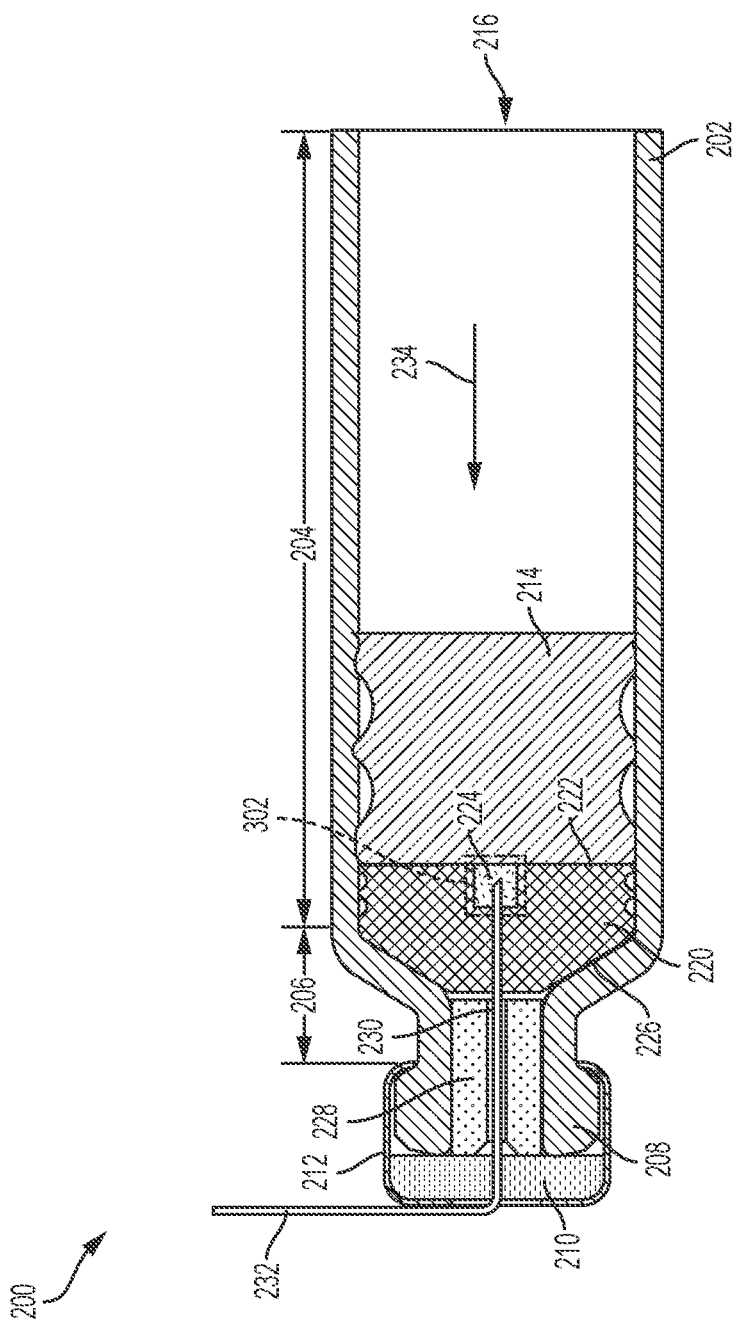
FIG. 3 illustrates a second view of the first exemplary drug delivery system.

FIG. 3 illustrates the drug delivery system 200 after expelling the liquid drug 218 from the cartridge 202. FIG. 3 can also represent a cross-sectional view of the drug delivery system 200. As shown in FIG. 3, the needle 232 is inserted through the needle insertion guide 228 and the cartridge stopper 220 such that the end of the needle 232 is maintained within the fluid path pocket 224. The needle 232 can have a shape (e.g., a bend) and length that ensures the end of the needle 232 is precisely positioned within the fluid path pocket 224 as shown. The plunger 214 is positioned against the first side 222 of the cartridge stopper 220 and does not contact the needle 232 or disturb the positioning of the needle 232. A hold-up volume 302 is shown in FIG. 3 as highlighting an approximate amount of the liquid drug 218 that remains inside the cartridge 202 (e.g., after no further liquid drug 218 can be expelled by the plunger 214). Comparing the hold-up volume 302 to the hold-up volume shown in FIG. 1B reveals that the drug delivery system 200 significantly reduces the amount of the liquid drug 218 that remains inside of the cartridge 202, while also improving dose delivery accuracy.

As shown in FIG. 3, with the addition of the cartridge stopper 220, a portion of the neck component 206 is blocked off, thereby reducing the resulting hold-up volume 302 as discussed above. Positioning the cartridge stopper 220 within the necked area of the cartridge 202 can provide a significant reduction in hold-up volume and increase in dose delivery accuracy. The positioning of the cartridge stopper 220 can also increase positional stability and provide space savings. Due to the reduced hold-up volume 302 provided by the drug delivery system 200, the drug delivery system 200 can deliver any air volume without affecting dose tolerance (e.g., if any air is trapped within the cartridge 202 and expelled by the plunger 214). This provides operational flexibility since the position of the plunger 214 does not need to be precisely controlled nor does any trapped air within the cartridge 202 need to be reduced to ensure accurate dosing of the liquid drug 218. Further, the smaller hold-up volume 302 reduces and minimizes any wasted or unused liquid drug 218 left within the cartridge 202. As previously mentioned, reducing the amount of wasted liquid drug 218 may reduce the cost of the drug delivery system 200 for a user.

The drug delivery system 200 can be sterilized prior to use and being provided to a user in a variety of manners. In various embodiments, the drug delivery system 200 can be sterilized with the needle 232 inserted between the septum 210 and the cartridge stopper 220 (e.g., as depicted in FIG. 2). Sterilization in this manner can provide a seal on the needle 232 and can maintain sterility thereafter. In various embodiments, the drug delivery system 200 can be sterilized with the needle 232 partially inserted in the cartridge stopper 220. Sterilization in this manner can also provide a seal on the needle 232 that can maintain sterility. In various embodiments, the drug delivery system 200 can be sterilized with the needle 232 completely removed from the cartridge 202 (i.e., separate from the cartridge assembly).

Figure 4:
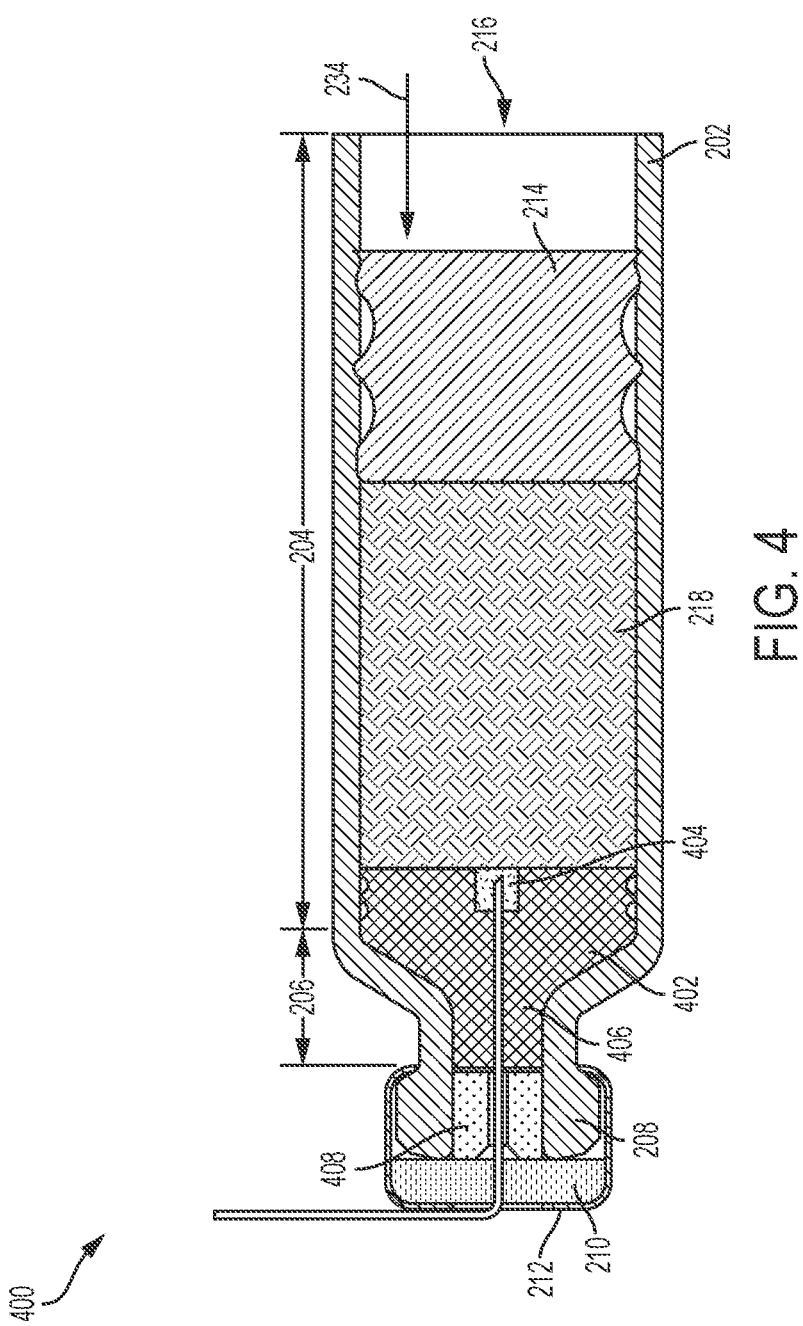
FIG. 4 illustrates a second exemplary drug delivery system.

FIG. 4 illustrates a second exemplary drug delivery system 400. The drug delivery system 400 is substantially similar to the drug delivery system 200 in design and operation and represents an alternative design to the drug delivery system 200. The drug delivery system 400 can provide substantially the same benefits as the drug delivery system 200 as described above. FIG. 4 can represent a cross-sectional view of the drug delivery system 400. In various embodiments, the drug delivery system 400 can provide a ratio of hold-up volume to fill volume that is less 5% or less than 3%.

As shown in FIG. 4, the drug delivery system 400 can include a cartridge stopper 402 having a fluid path pocket 404 on a first side and a second side having an extended portion 406. The extended portion 406 can extend further into the neck component 206 of the cartridge 202. As also shown in FIG. 4, a needle insertion guide 408 of the drug delivery system 400 can be substantially arranged and positioned within the top component 208 of the cartridge 202. This alternative design and arrangement of the cartridge stopper 402 and the needle insertion guide 408 (e.g., in comparison to the cartridge stopper 220 and the needle insertion guide 228, respectively) can provide increased sealing capabilities and additional stability for the needle 232. In general, for any of the drug delivery systems described herein that provide reduced hold-up volume, the cartridge stopper (e.g., the cartridge stopper 220 or 402) and the needle insertion guide (e.g., the needle insertion guide 228 and 408) can be of any size and shape and can occupy any portions of the main body 204, the neck component 206, and/or the top component 208.

Figure 5:
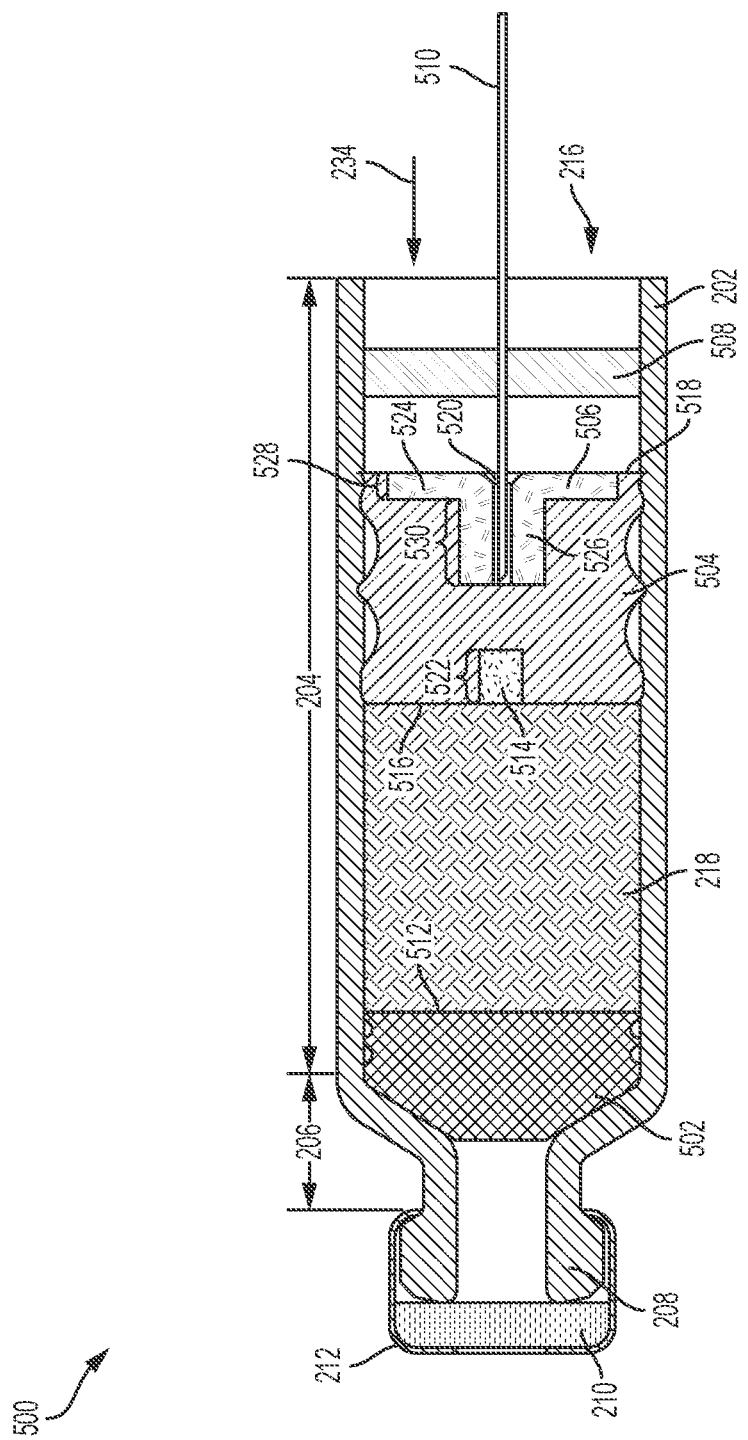
FIG. 5 illustrates a first view of a third exemplary drug delivery system.

FIG. 5 illustrates a third exemplary drug delivery system 500 for providing a reduced hold-up volume. As a result, the drug delivery system 500 provides efficient delivery of a stored liquid drug. FIG. 5 can represent a cross-sectional view of the drug delivery system 500. In various embodiments, the drug delivery system 500 can provide a ratio of hold-up volume to fill volume that is less 5% or less than 3%.

As shown in FIG. 5, the drug delivery system 500 can include many of the components depicted and described in relation to the drug delivery system 200 and can further include a cartridge stopper 502, a plunger 504, a needle insertion guide 506, an optional secondary needle seal 508, and a needle 510. The cartridge stopper 502 can be positioned within a portion of the main body component 204 and the neck component 206. The cartridge stopper 502 can have a first side 512 that is substantially planar or flat that can be coupled to the liquid drug 218. The cartridge stopper 502 can provide a first seal for the liquid drug 218 for containment within the cartridge 202. The cartridge stopper 502 can be generally cylindrical-shaped and can be formed of any suitable material such as, for example, a plastic or rubber.

The plunger 504 can be positioned within the main body component 204. The plunger 504 can include a fluid path pocket 514. The fluid path pocket 514 can comprise a hole or opening that extends partially into the plunger 504 from a first side or surface 516 of the plunger 504. The fluid path pocket 514 can be round or cylindrical in shape and can be centered about the plunger 504 (e.g., about a central axis of the plunger 504). The plunger 504 can form a second seal for the liquid drug 218 for containment within the cartridge 202. The plunger 504 can be generally cylindrical-shaped and can be formed of any suitable material such as, for example, a plastic or rubber.

The needle insertion guide 506 can be positioned into the plunger 504 from a second side or surface 518 of the plunger 504. In this way, the plunger 504 can provide stability for the needle insertion guide 506. The needle insertion guide 506 can include an opening or hole 520 that extends through the needle insertion guide 506. The opening 520 can be aligned with the fluid path pocket 514 and can provide a guide for stabilizing and orienting the needle 510. Specifically, the needle insertion guide 506 can ensure that an end of the needle 510 can be positioned within the fluid path pocket 514 when the needle 510 is moved further in the direction 234. The needle insertion guide 506 can comprise any suitable material such as, for example, metal, stainless steel, plastic, or a polymer, or any combination thereof.

The optional secondary needle seal 508 can be positioned in the main body component 204 between the plunger 504 and needle insertion guide 506 and an end of the cartridge 202. The optional secondary needle seal 508 can comprise any suitable materials such as, for example, rubber, plastic, or a polymer, or any combination thereof. The optional secondary needle seal 508 can provide a seal for the needle 510 for sterilization.

FIG. 5 can represent the drug delivery system 500 prior to activation or initiation of expelling the stored liquid drug 218. When activated, the end of the needle 510 can be positioned in the fluid path pocket 514 by having the needle 510 move in the direction 234. The needle 510 can pierce and traverse a portion of the plunger 504 between the needle insertion guide 506 and the fluid path pocket 514 in order to reach the fluid path pocket 514.

Once the end of the needle 510 is positioned within the fluid path pocket 514, the plunger 504 (and the needle insertion guide 506 and the needle 506) can be moved in the direction 234. As the plunger 504 is moved towards the cartridge stopper 502, the liquid drug 218 can be expelled out of the cartridge 202 through the needle 510. The drug delivery system 500 enables the liquid drug 218 to be expelled out of an opposite end of the cartridge 202 as compared to the end of the cartridge 202 from which the liquid drug 218 is expelled by the drug delivery system 200.

As described above, the fluid path pocket 514 can be positioned within a center of the plunger 504. The fluid path pocket 514 can have any cross-sectional shape such as, for example, circular or rectangular. The fluid path pocket 514 can have a depth 522—that is, the fluid path pocket 514 can extend a distance 522 into the plunger 504 from the first surface 516 of the plunger 504.

The needle insertion guide 506 can include a base component 524 and an extension component 526. The base component 524 can extend into the plunger 504 by a first distance 528 and the extension component 526 can extend into the plunger 504 by an additional second distance 530 beyond the first distance 528. The base component 524 can be substantially flush with the second surface 518 of the plunger 506.

In various embodiments, the needle insertion guide 506 can be arranged and/or shaped in different manners. For example, the needle insertion guide 506 can be positioned adjacent to the second surface 518 of the plunger 502 rather than being inserted into a portion of the plunger 504. In such embodiments, the needle insertion guide 506 may be substantially cylindrical having a substantially uniform thickness.

Figure 6:
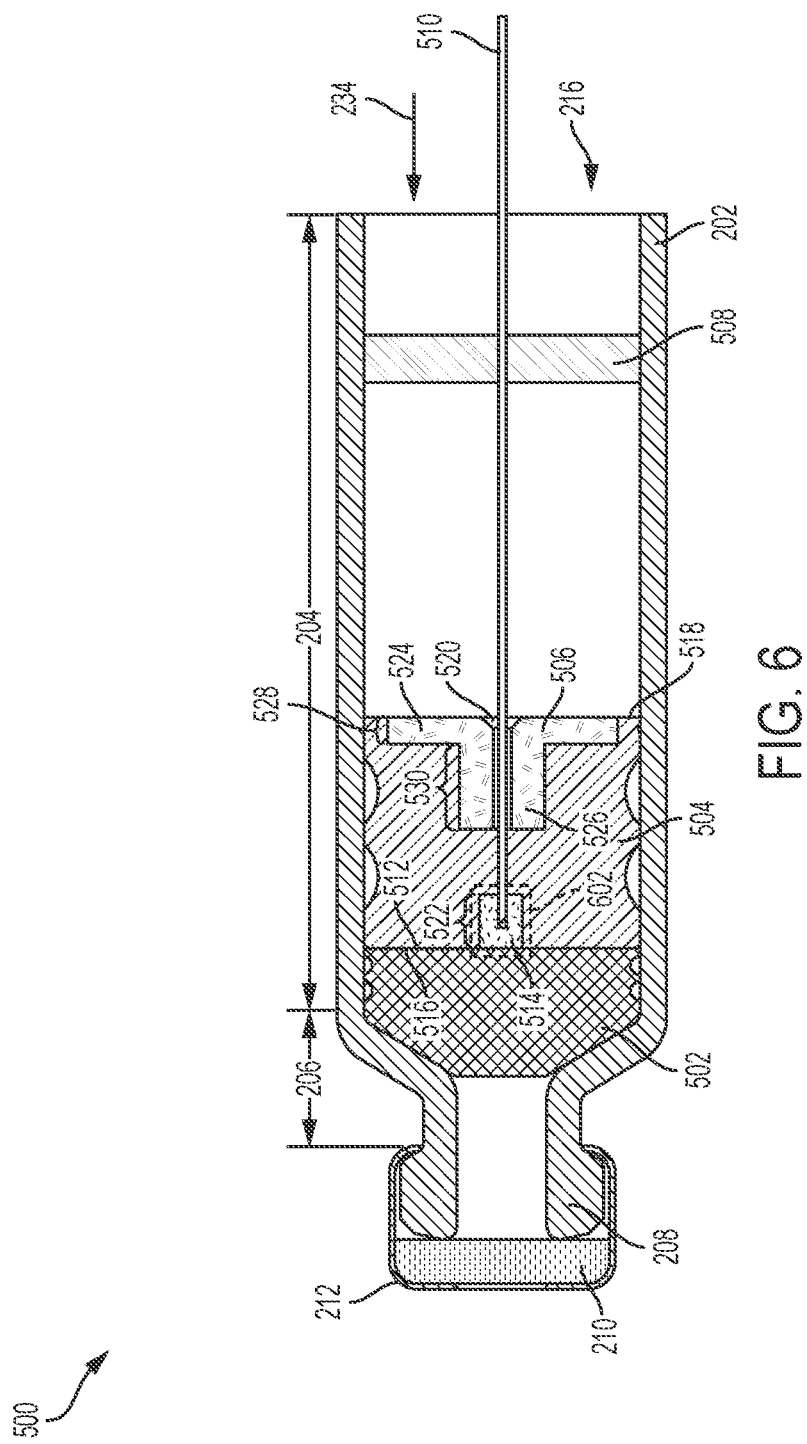
FIG. 6 illustrates a second view of the third exemplary drug delivery system.

FIG. 6 illustrates the drug delivery system 500 after expelling the liquid drug 218 from the cartridge 202. FIG. 6 can also represent a cross-sectional view of the drug delivery system 500. As shown in FIG. 6, the needle 510 is inserted through the needle insertion guide 506 and the plunger 504 such that the end of the needle 510 is maintained within the fluid path pocket 514. The plunger 504 is positioned against the first side 512 of the cartridge stopper 502 without the cartridge stopper 502 contacting the needle 510 or disturbing the positioning of the needle 510. A hold-up volume 602 is shown in FIG. 6 as highlighting an approximate amount of the liquid drug 218 that remains inside of the cartridge 202. Comparing the hold-up volume 602 to the hold-up volume shown in FIG. 1B reveals that the drug delivery system 500 significantly reduces the amount of the liquid drug 218 that remains inside of the cartridge 202, while also improving dose delivery accuracy.

The drug delivery system 500 can be sterilized prior to use and being provided to a user in a variety of manners. In various embodiments, the drug delivery system 500 can be sterilized with the needle 510 positioned within the needle insertion guide 506 but not coupled to the liquid drug 218. In such embodiments, the optional secondary needle seal 508 can be used to maintain sterility of the needle 510 from the end positioned in the needle insertion guide 506 to the portion of the needle 510 adjacent the optional secondary needle seal 508. In various embodiments, the drug delivery system 500 can be sterilized with the needle 510 partially inserted into the plunger 504 (e.g., with the end of the needle 510 positioned in the plunger 504 prior to reaching the fluid path pocket 514). In various embodiments, the drug delivery system 500 can be sterilized with the needle 510 inserted into the fluid path pocket 514 and coupled to the liquid drug 518. In such embodiments, a needle seal at the opposite end of the needle can be used to seal the needle path.

The drug delivery system 500, by incorporating rear piercing of the plunger 504, can reduce the overall size of the drug delivery system 500 by obviating the need for delivery mechanisms positioned near a front end of the cartridge 202 (e.g., near the top component 208). In various embodiments, the drug delivery system 500, as depicted in FIGS. 5 and 6, can provided without the septum 210 and the crimp 212.

Figure 7:
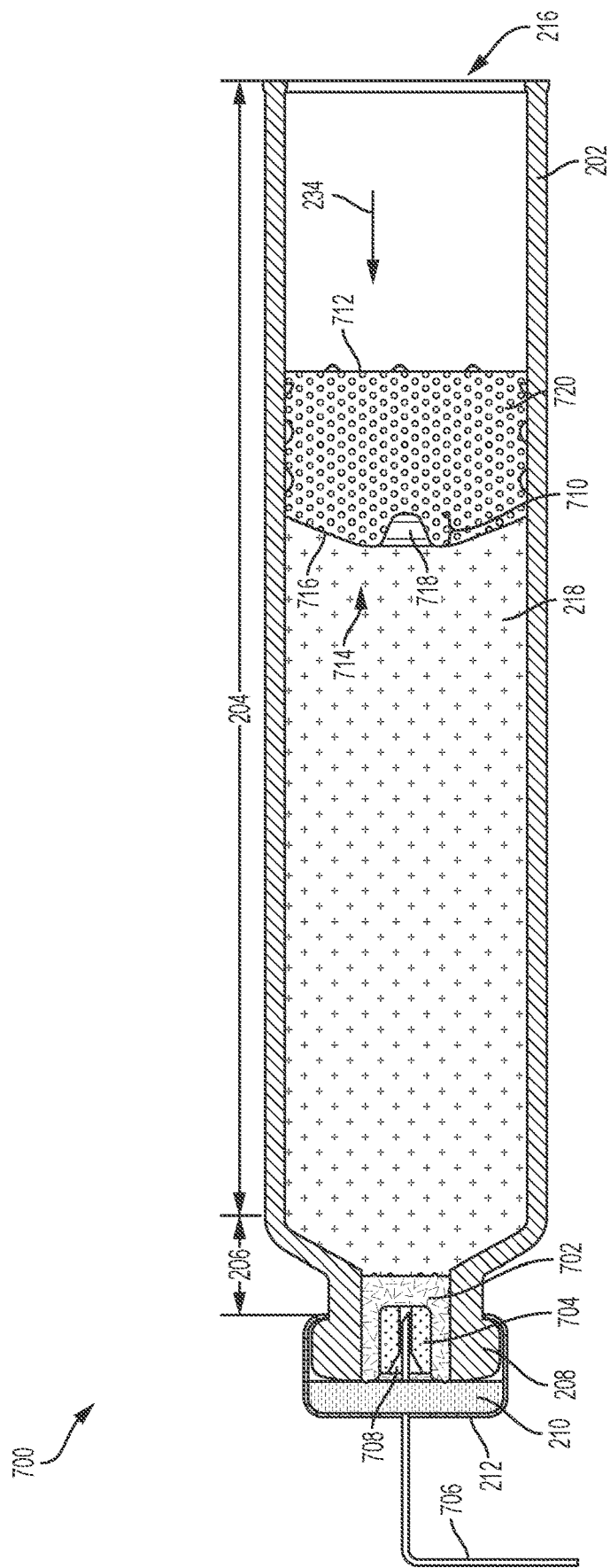
FIG. 7 illustrates a first view of a fourth exemplary drug delivery system.

FIG. 7 illustrates a fourth exemplary drug delivery system 700. The drug delivery system 700 can include certain features that are substantially similar to the drug delivery system 200 as shown. The drug delivery system 700 can operate in a similar manner to the drug delivery system 200 while representing an alternative design to the drug delivery system 200. The drug delivery system 700 can provide substantially the same benefits as the drug delivery system 200 as described above. FIG. 7 can represent a cross-sectional view of the drug delivery system 700. In various embodiments, the drug delivery system 700 can provide a ratio of hold-up volume to fill volume that is less 5% or less than 3%.

As shown in FIG. 7, the drug delivery system 700 includes a cartridge stopper 702. The cartridge stopper 702 can be formed from any suitable material such as, for example, plastic or rubber. The cartridge stopper 702 can be positioned with a portion of the neck component 206 and/or the top component 208. In various embodiments, the cartridge stopper 702 can be positioned so as not to extend beyond the position of the neck component 206 having a substantially constant diameter (i.e., to not be positioned within the transition region of the neck component 206). The cartridge stopper 702 can be cylindrically-shaped to tightly fit within the diameter of the neck component 208 (e.g., the smallest diameter of the cartridge 202). In various embodiments, the cartridge stopper 702 can be positioned within the neck component 208 using an interference fit or press fit. The cartridge stopper 702 can help seal the liquid drug 218 within the cartridge 202 such that, for example, the liquid drug 218 does not contact the septum 210. As shown in FIG. 7, the arrangement and positioning of the cartridge stopper 702 allows a portion of the liquid drug to extend into the neck component 206 of the cartridge 202.

The drug delivery system 700 can further include a needle insertion guide component 704. The needle insertion guide component 704 can be positioned within the cartridge stopper 702. In various embodiments, the cartridge stopper 702 can have an opening (e.g., a partially hollow center portion or cavity) that allows the needle insertion guide component 704 to be positioned into the cartridge stopper 702 to be tightly sealed and retained therein. The needle insertion guide component 704 can be formed of any suitable material such as, for example, metal, stainless steel, rubber, plastic, or a polymer, or any combination thereof. The needle insertion guide component 704 can be cylindrically-shaped and can be positioned entirely within the cartridge stopper 702.

A needle 706 can be positioned with the needle insertion guide component 704. The needle insertion guide component 704 can include an opening or hole 708 that extends the length of the needle insertion guide component 704. The needle 706 can be positioned within the opening 708. The opening 708 can provide a guide for the needle 706. The opening 708 can have a first conical portion (positioned closer to the top component 208) and a cylindrical portion (positioned closer to the main body component 204) as shown in FIG. 7. The opening 708 can be positioned along a center of the needle insertion guide component 704 (e.g., along a central axis of the needle insertion guide component 704).

The drug delivery system 700 can further include a plunger 720. The plunger 720 can be formed of any suitable material such as, for example, plastic or rubber. The plunger 720 can form another seal for the liquid drug 218. The liquid drug 218 can be accessed by the needle 706. Specifically, the needle 706 can be moved to pierce the cartridge stopper 702 to access the liquid drug 218. After piercing the cartridge stopper 702 to access the liquid drug 218, an end of the needle 706 can be positioned within the neck component 206 in fluid communication with the liquid drug 218.

As shown, the plunger 720 can have a first side or surface 712 and a second side or surface 714. The first side 712 can be substantially planar or flat and can face the opening 216 of the cartridge 202. The second side 714 can have a surface 716 that extends at an angle from a side of the plunger 720. The side of the plunger 720 can include one or more seal features and can be substantially cylindrical in shape. The surface 716 can extend from the side of the plunger 720 at an angle to a fluid path pocket area or component 718. The second surface 714 of the plunger 720 can be shaped to approximately match a shape of the neck component 206—in particular, a transition region of the neck component 206.

The fluid path pocket 718 can be a hole or opening that extends into the plunger 720 (e.g., partially into the plunger 720 from the second side 714) by a distance or depth 710. The fluid path pocket 718 can have any shape such as, for example, circular or square. The fluid path pocket 718 can have a decreasing diameter moving in a direction from the second side 714 to the first side 712. The fluid path pocket 718 can be positioned about a center of the plunger 720 (e.g., along a central axis of the plunger 720).

The fluid path pocket 718 can be aligned with the opening 708 of the needle insertion guide component 704. In this way, when the needle 706 pierces through the cartridge stopper 702 and is coupled to the liquid drug 218, an end of the needle 706 will align with the fluid path pocket 718. This enables the plunger 720 to be pushed into the transition area of the neck component 206 without damaging the needle 706 or its position, as the end of the needle 706 is secured within the fluid path pocket 718 and does not contact the plunger 720. Precise positioning of the end of the needle 706 can be controlled by a number of manners including, for example, a shape of the needle 706—for example, by including a bend or turn in the needle 706 to limit how far the needle 706 can extend into the cartridge 202.

To expel the liquid drug 218 from the cartridge 202, the plunger 720 can be advanced in the direction 234 toward the cartridge stopper 702. As the plunger 720 is advanced, the liquid drug 218 can be forced out of the cartridge 202 through the needle 706.

As shown in FIG. 7, the cartridge stopper 702 blocks off a portion of the neck component 206. The size, arrangement, and positioning of the cartridge stopper 702, along with the shape of the plunger 720, can provide reduced hold-up volume and an increase in dose delivery accuracy. Further, the cartridge 202 can be filled using standard fill and finishing processes with standardized equipment and can be filled with the liquid drug from the opening 216 (e.g., before installing the plunger 720). Compared to the drug delivery system 200, the drug delivery system 700 can be made shorter in length while holding and delivering the same amount of liquid drug 218. As a result, an on-body delivery system (e.g., an insulin pump) holding the drug delivery system 700 can be made shorter in length.

In various embodiments, the cartridge stopper 702 can be considered as including a central opening or cavity for accepting the needle guide component 704. The needle guide component 704 can be tightly pressed or fitted into the cavity of the cartridge stopper 702, so that the cartridge stopper 702 is tightly positioned around the needle guide component 704 and against the cartridge 202 to form a seal for the liquid drug 218.

The cartridge stopper 702 can be considered to be disposed or positioned within a first region or portion of the cartridge 202. This first region or portion of the cartridge 202 can have a first diameter. In contrast, the plunger 720 can be considered to be positioned within a second region or portion of the cartridge 202. This second region or portion of the cartridge 202 can have a second diameter, with the second diameter being larger than the first diameter. The cartridge 202 can further include a region or portion where the cartridge 202 transitions from the first diameter to the second diameter. As shown in FIG. 7, the plunger 720 can be shaped to approximately match the boundaries of this transition region. Further, the diameter of the cartridge stopper 702 can approximately match the first diameter of the cartridge 202 and the diameter of the plunger 720 can approximately match the second diameter of the cartridge 202.

In various embodiments, as further described herein, the opening 708 of the needle guide component 704 can be aligned with the fluid path pocket 718. In various embodiments, the opening 708 can be aligned with a center of the fluid path pocket 718. In various embodiments, the opening 718 and the fluid path pocket 718 can be aligned and/or centered about a same central axis of either component and/or the cartridge 202.

Figure 8:
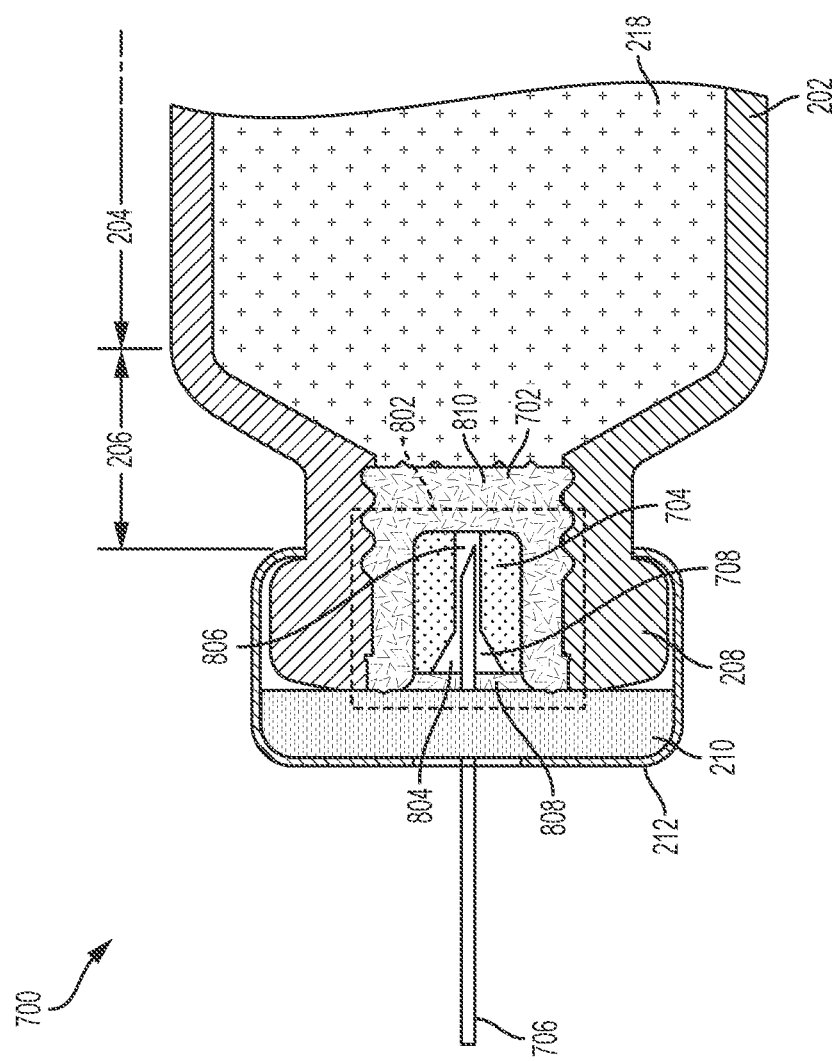
FIG. 8 illustrates a second view of the fourth exemplary drug delivery system.

FIG. 8 illustrates a close-up view of a portion of the drug delivery system 700. As shown in FIG. 8, the needle 706 can be stored in the position show—that is, the needle 706 can be positioned within the needle insertion guide component 704 without piercing the cartridge stopper 702 so as to access the liquid drug 218. When the drug delivery system 700 is activated, a needle insertion mechanism (not shown in FIG. 8) can advance the needle 706 into the neck component 206 to be coupled with the liquid drug 218.

A sterile zone 802 represents a sterile area of the drug delivery system 700. The needle 706, as shown, can be stored prior to activation of the drug delivery system 700 within the sterile zone 802. The drug delivery system 700 can be sterilized after the needle 706 is inserted into the position as shown in FIG. 8. The sterile zone 802 can remain sealed and sterile prior to use.

As further shown in FIG. 8, the opening 708 of the needle insertion guide component 704 can include a first conical portion 804 (positioned closer to the top component 208) and a second cylindrical portion 806 (positioned closer to the main body component 204). The needle insertion guide component 704 can be fully positioned within an inner portion (e.g., opening) of the cartridge stopper 702.

The cartridge stopper 702 can include a first portion 808 (positioned adjacent to the septum 210) and a second portion 810 (positioned adjacent to the liquid drug 218). During storage and/or prior to activation of the drug delivery system 700, the needle 706 can be positioned as shown in FIG. 8—for example, positioned through the first portion 808 and adjacent to the second portion 810 (but not yet having pierced the second portion 810). The needle 706 can be advanced toward the second portion 810 and can pierce the second portion 810 when the drug delivery system 700 is activated, thereby coupling the needle 706 to the liquid drug 218. The needle insertion guide component 704 can provide accurate guiding of needle 706 through the cartridge stopper 702.

Figure 9:
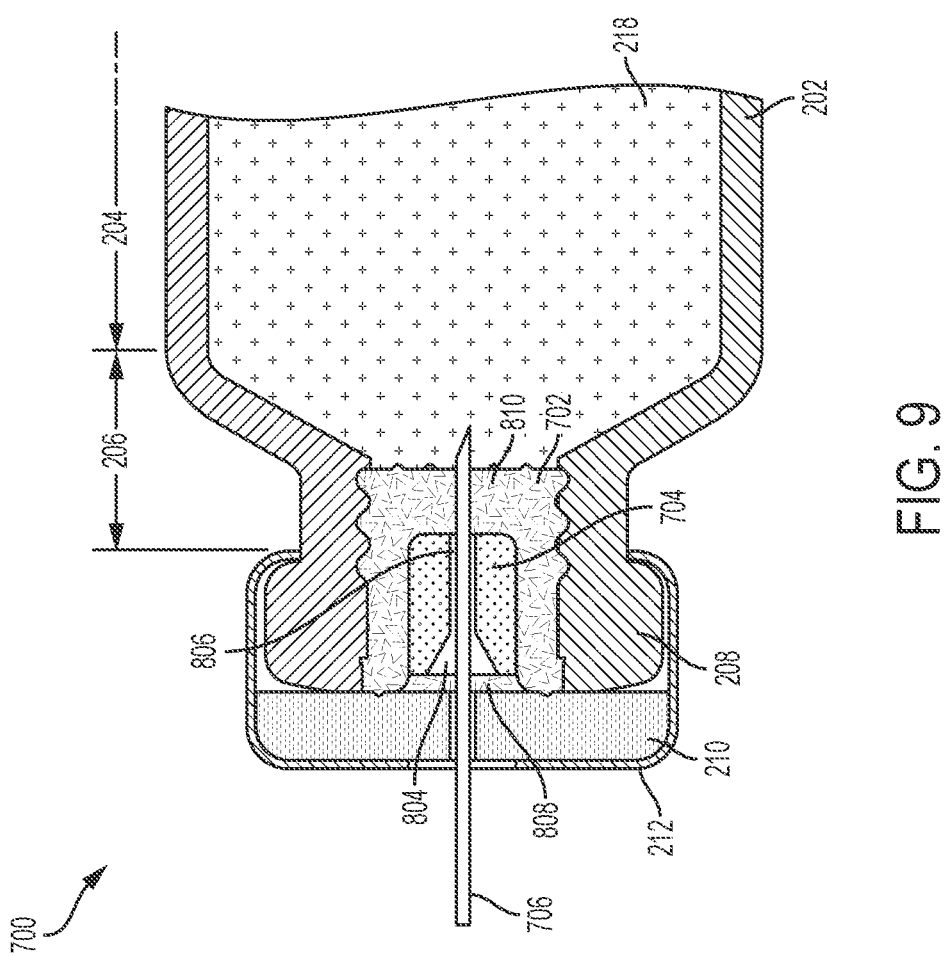
FIG. 9 illustrates a third view of the fourth exemplary drug delivery system.

FIG. 9 illustrates the drug delivery system 700 after activation. Specifically, FIG. 9 illustrates the drug delivery system 700 after the needle 706 has been advanced toward the liquid drug 218. FIG. 9 also illustrates a close-up view of a portion of the drug delivery system 700. As the needle 706 is advanced, the end of the needle 706 pierces and extends through the second portion 810 of the cartridge stopper 702. The end of the needle 706 extends just beyond the cartridge stopper 702 and is coupled to the liquid drug 218. The needle insertion guide component 704 provides accurate alignment of the needle 706 through the cartridge stopper 706 (e.g., to maintain alignment of the needle 706 with the central axis of the cartridge stopper 706).

Once the needle 706 is advanced into the cartridge 202 as shown in FIG. 9, the plunger 720 (as shown in FIG. 7) can be advanced in the direction 234 to expel the liquid drug 218 out of the cartridge 202 through the needle 706. In various embodiments, the thickness of the second portion 810 of the cartridge stopper 702 can maintain sterility and non-permeability prior to being pierced by the needle 706. For example, the second portion 810 of the cartridge stopper 706 can have a thickness of at least 1.5 mm to maintain closure integrity of the container 202.

Figure 10:
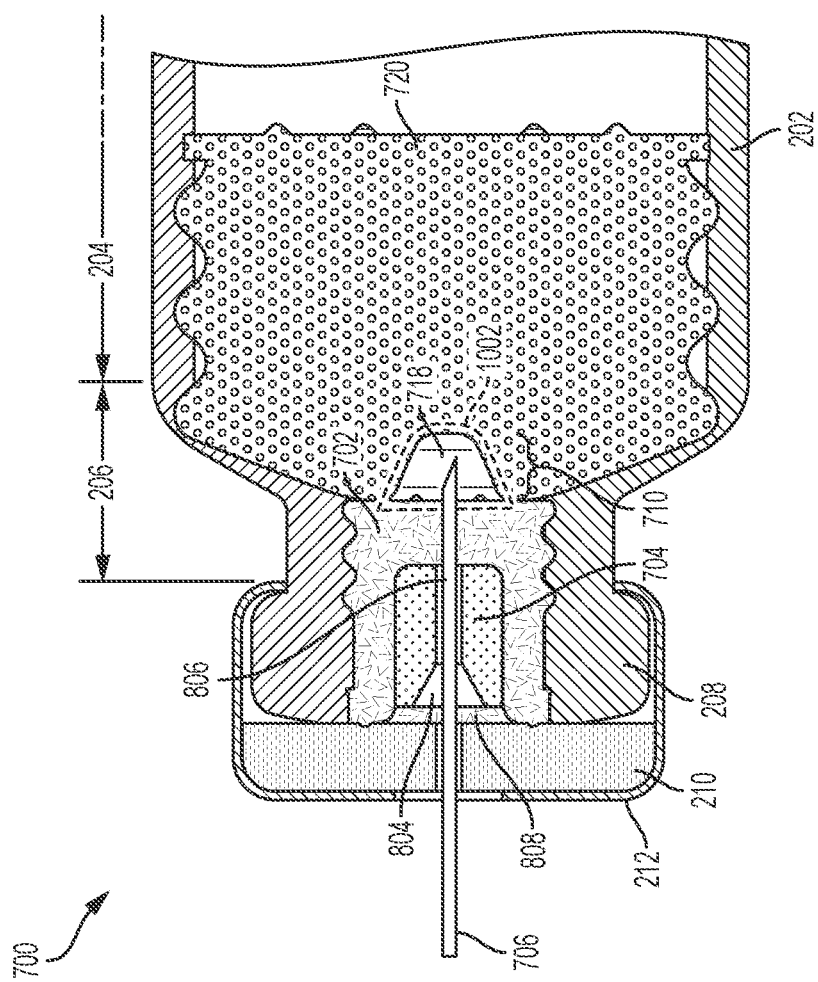
FIG. 10 illustrates a fourth view of the fourth exemplary drug delivery system.

FIG. 10 illustrates the drug delivery system 700 after substantially all of the liquid drug 218 has been expelled from the cartridge 202. FIG. 10 also illustrates a close-up view of a portion of the drug delivery system 700. As shown, the end of the needle 706 is positioned within the fluid path pocket 718. The needle insertion guide component 704 ensures the end of the needle 706 is aligned with the fluid path pocket 718. The plunger 720 is positioned against the cartridge stopper 702. The plunger 720 is also pressed against the neck component 206 such that the surface 716 is pressed against the transitional portion of the neck component 206—with a portion of the surface 716 surrounding the fluid path pocket 718 adjacent to or pressed against the cartridge stopper 702 as shown.

A hold-up volume 1002 is shown in FIG. 10 as highlighting an approximate amount of the liquid drug 218 that remains inside of the cartridge 202. Comparing the hold-up volume 1002 to the hold-up volume of FIG. 1B reveals that the drug delivery system 700 significantly reduces the amount of the liquid drug 218 that remains inside of the cartridge 202, while also improving dose delivery accuracy.

The positioning of the needle 706, in terms of concentricity (e.g., with respect to the cartridge 202) and depth (e.g., with respect to the neck component 206) can be controlled to leave a relatively small hold-up volume 1002. As further shown, the needle 706 is positioned such that at the end of the plunger stroke (e.g., when the plunger 720 is positioned as far against the neck component 206 as possible), the needle 706 remains in the fluid path pocket 718.

The drug delivery system 700 provides further advantages in that the drug delivery system 700 provides a reduced amount of surface area from the cartridge stopper 702 and the plunger 720 that may contact the liquid drug 218 (e.g., in comparison to the other drug delivery systems described herein that have larger combined surface areas in contact with the liquid drug 218 due to the increased surface area of the cartridge stoppers used therein). In various embodiments, the cartridge stopper 702 and the plunger 720 can be formed from an elastomer. Leachable and extractable levels of a drug can result when a liquid drug is in contact with an elastomer, which can adversely affect the drug and/or adversely affect drug stability. Accordingly, the reduced surface area of the cartridge stopper 702 and the plunger 720 (e.g., combined or in total) provided by the drug delivery system 700 can improve stability of the liquid drug 218.

Any of the individual drug delivery systems described herein (e.g., drug delivery systems 200, 400, 500, and 700) and/or any features thereof can be combined with any other drug delivery system and/or feature thereof.

The following examples pertain to additional further embodiments:

Example 1 is a drug delivery system comprising a cartridge configured to hold a liquid drug, a cartridge stopper positioned in a first portion of the cartridge having a first diameter, a needle guide component positioned within the cartridge stopper, a needle positioned within a central opening of the needle guide, and a plunger positioned in a second portion of the cartridge having a second diameter, the second diameter larger than the first diameter, the plunger having a fluid path pocket facing and aligned with the central opening of the needle guide component.

Example 2 is an extension of example 1 or any other example disclosed herein, wherein the cartridge is an International Organization for Standardization (ISO) cartridge.

Example 3 is an extension of example 1 or any other example disclosed herein, wherein the cartridge stopper is formed from plastic or rubber Example 4 is an extension of example 1 or any other example disclosed herein, wherein the cartridge stopper is cylindrically-shaped.

Example 5 is an extension of example 4 or any other example disclosed herein, wherein the cartridge stopper has a diameter approximately matching the first diameter, the cartridge stopper configured to form a seal for the liquid drug.

Example 6 is an extension of example 5 or any other example disclosed herein, wherein the cartridge stopper includes a central cavity configured to retain the needle guide component.

Example 7 is an extension of example 6 or any other example disclosed herein, wherein the needle guide component is formed from metal, plastic, or rubber.

Example 8 is an extension of example 7 or any other example disclosed herein, wherein the needle guide component is configured to be fitted within the central cavity of the cartridge stopper.

Example 9 is an extension of example 8 or any other example disclosed herein, wherein the central opening of the needle guide component includes a conical portion and a cylindrical portion.

Example 10 is an extension of example 9 or any other example disclosed herein, wherein the cylindrical portion is positioned closer to the plunger.

Example 11 is an extension of example 10 or any other example disclosed herein, wherein the central opening of the needle guide component is aligned with a central axis of the needle guide component.

Example 12 is an extension of example 11 or any other example disclosed herein, wherein the central opening of the needle guide component is aligned with a center of the fluid path pocket.

Example 13 is an extension of example 1 or any other example disclosed herein, wherein the plunger includes a first surface facing an opening of the cartridge and a second surface facing the cartridge stopper, the second surface containing the fluid path pocket, the plunger forming a seal for the liquid drug.

Example 14 is an extension of example 13 or any other example disclosed herein, wherein the first surface is substantially planar.

Example 15 is an extension of example 13 or any other example disclosed herein, wherein the plunger has a diameter approximately matching the second diameter.

Example 16 is an extension of example 13 or any other example disclosed herein, wherein the fluid path pocket is cylindrically-shaped.

Example 17 is an extension of example 13 or any other example disclosed herein, wherein the fluid path pocket has a depth that extends into the plunger from the second surface.

Example 18 is an extension of example 17 or any other example disclosed herein, wherein the fluid path pocket comprises a decreasing diameter along the depth of the fluid path pocket.

Example 19 is an extension of example 17 or any other example disclosed herein, wherein the second surface is angled from a side of the plunger toward the fluid path pocket.

Example 20 is an extension of example 19 or any other example disclosed herein, wherein the second surface is shaped to approximately match a transition region of the cartridge, the transition region of the cartridge having a variable diameter that transitions from the first diameter to the second diameter.

Example 21 is an extension of example 13 or any other example disclosed herein, wherein the needle is configured to pierce the cartridge stopper to be coupled to the liquid drug.

Example 22 is an extension of example 21 or any other example disclosed herein, wherein the plunger is configured to be driven toward the cartridge stopper to expel the liquid drug out of the cartridge through the needle.

Example 23 is an extension of example 22 or any other example disclosed herein, wherein an end of the needle is configured to be positioned within the fluid path pocket of the plunger when the plunger expels substantially all of the liquid drug from the cartridge.

Example 24 is an extension of example 22 or any other example disclosed herein, wherein an end of the needle is configured to be positioned within the fluid path pocket of the plunger when the second surface of the plunger is pressed against the cartridge stopper.

Example 25 is an extension of example 24 or any other example disclosed herein, wherein the end of the needle is not in contact with the plunger.

Example 26 is an extension of example 1 or any other example disclosed herein, wherein the needle guide component is formed from a metal.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A drug delivery system, comprising:
   a cartridge configured to hold a liquid drug;
   a cartridge stopper positioned in a first portion of the cartridge and including a fluid path pocket;
   a needle insertion guide positioned adjacent to the cartridge stopper, wherein:
   the needle insertion guide has an opening aligned with the fluid path pocket,
   the opening extends along an entire length of the needle insertion guide, and
   the opening includes a conical portion and a cylindrical portion; and
   a plunger positioned in a second portion of the cartridge and operable to advance through the cartridge in a direction of the cartridge stopper.

2. The drug delivery system of claim 1, wherein the cartridge stopper is formed from plastic or rubber.

3. The drug delivery system of claim 1, wherein the cartridge stopper is cylindrically-shaped.

4. The drug delivery system of claim 1, wherein the cartridge stopper has a shape operable to fit within a transition region of a neck component of the cartridge, and the cartridge stopper is operable to form a seal for the liquid drug.

5. The drug delivery system of claim 1, wherein the needle insertion guide is formed from metal, plastic, or rubber.

6. The drug delivery system of claim 1, wherein the plunger includes a first surface facing the cartridge stopper and a second surface facing an opening of the cartridge, the first surface positioned to contact a liquid drug in the cartridge, and the plunger forms a seal with the cartridge for the liquid drug.

7. The drug delivery system of claim 6, wherein the first surface of the plunger and the second surface of the plunger are substantially planar.

8. The drug delivery system of claim 1, wherein the fluid path pocket is cylindrically-shaped.

9. The drug delivery system of claim 1, wherein the cartridge stopper has a second side angled to match a neck component of the cartridge.

10. The drug delivery system of claim 1, wherein the cartridge stopper has a second side and the fluid path pocket has a depth that extends into the cartridge stopper from a first side.

11. The drug delivery system of claim 1, further comprising:
    a needle operable to deliver a liquid drug, wherein the needle is positioned within an opening of the needle insertion guide and operable to reach the fluid path pocket when inserted into the cartridge and through the cartridge stopper to the fluid path pocket.

12. The drug delivery system of claim 11, wherein the needle further comprises:
    a shape and a length operable to position an end of the needle within the fluid path pocket.

13. The drug delivery system of claim 12, wherein the plunger when positioned against a first side of the cartridge stopper does not contact or disturb the positioning of the needle.

14. The drug delivery system of claim 11, wherein the plunger includes a first surface facing the cartridge stopper and an end of the needle is configured to be positioned within the fluid path pocket of the cartridge stopper when the first surface of the plunger contacts the cartridge stopper.

15. The drug delivery system of claim 1, wherein the plunger is configured to be driven toward the cartridge stopper to expel the liquid drug out of the cartridge through the needle.

16. The drug delivery system of claim 1, further comprising:
    a crimp and a septum, wherein the crimp is positioned around the septum and a top component of the cartridge and is operable to tightly fit the septum against the top component.

17. The drug delivery system of claim 16, wherein the crimp and septum are positioned over an opening to the needle insertion guide and are operable to be pierced by a needle during insertion of the needle into the needle insertion guide.

18. The drug delivery system of claim 16, wherein the needle insertion guide is positioned between the septum and the cartridge stopper.

* * * * *